(12) United States Patent
Valia et al.

(10) Patent No.: US 9,539,201 B2
(45) Date of Patent: Jan. 10, 2017

(54) SELEGILINE TRANSDERMAL SYSTEM

(71) Applicant: KAT Transdermals LLC, Kendall Park, NJ (US)

(72) Inventors: Kirti H. Valia, Plainsboro, NJ (US); Thomas Mark Rossi, Stockton, NJ (US); Agis Kydonieus, Kendall Park, NJ (US)

(73) Assignee: KAT Transdermals LLC, Kendall Park, NJ (US)

( * ) Notice: Subject to any disclaimer, the term of this patent is extended or adjusted under 35 U.S.C. 154(b) by 446 days.

(21) Appl. No.: 13/866,278

(22) Filed: Apr. 19, 2013

(65) Prior Publication Data

US 2013/0281542 A1    Oct. 24, 2013

Related U.S. Application Data

(60) Provisional application No. 61/687,215, filed on Apr. 20, 2012.

(51) Int. Cl.
| | | |
|---|---|---|
| *A61K 9/14* | (2006.01) | |
| *A61K 31/137* | (2006.01) | |
| *A61K 9/00* | (2006.01) | |
| *A61K 9/70* | (2006.01) | |

(52) U.S. Cl.
CPC .......... *A61K 9/0014* (2013.01); *A61K 9/7061* (2013.01); *A61K 31/137* (2013.01)

(58) Field of Classification Search
CPC ... A61K 31/137; A61K 9/0014; A61K 9/7061
See application file for complete search history.

(56) References Cited

U.S. PATENT DOCUMENTS

| | | |
|---|---|---|
| 6,239,181 B1 | 5/2001 | Bobotas |
| 6,461,619 B1 | 10/2002 | Resnick |
| 6,709,664 B2 | 3/2004 | Resnick |
| 6,974,588 B1 | 12/2005 | Miranda et al. |
| 7,045,145 B1 | 5/2006 | Chien |
| 7,070,808 B2 | 7/2006 | Govil et al. |
| 7,147,864 B2 | 12/2006 | Resnick |
| 7,150,881 B2 | 12/2006 | Govil et al. |
| 7,638,140 B2 | 12/2009 | Govil et al. |
| 2001/0023260 A1 | 9/2001 | Bobotas |
| 2002/0150613 A1 | 10/2002 | Govil et al. |
| 2007/0212428 A1 | 9/2007 | Wittlin |
| 2008/0220092 A1 | 9/2008 | Dipierro et al. |
| 2010/0087768 A1 | 4/2010 | Forlano et al. |
| 2010/0280432 A1 | 11/2010 | Dipierro et al. |

FOREIGN PATENT DOCUMENTS

| | | |
|---|---|---|
| WO | 2009009649 A1 | 1/2009 |
| WO | 2009009651 A1 | 1/2009 |

*Primary Examiner* — Sreeni Padmanabhan
*Assistant Examiner* — Jody Karol
(74) *Attorney, Agent, or Firm* — Hoffman Warnick LLC

(57) ABSTRACT

Embodiments of the invention relate generally to the field of transdermal delivery and more specifically to transdermal patches containing selegiline base for the treatment of depression, Parkinson's disease, and other nervous system conditions.

6 Claims, 5 Drawing Sheets

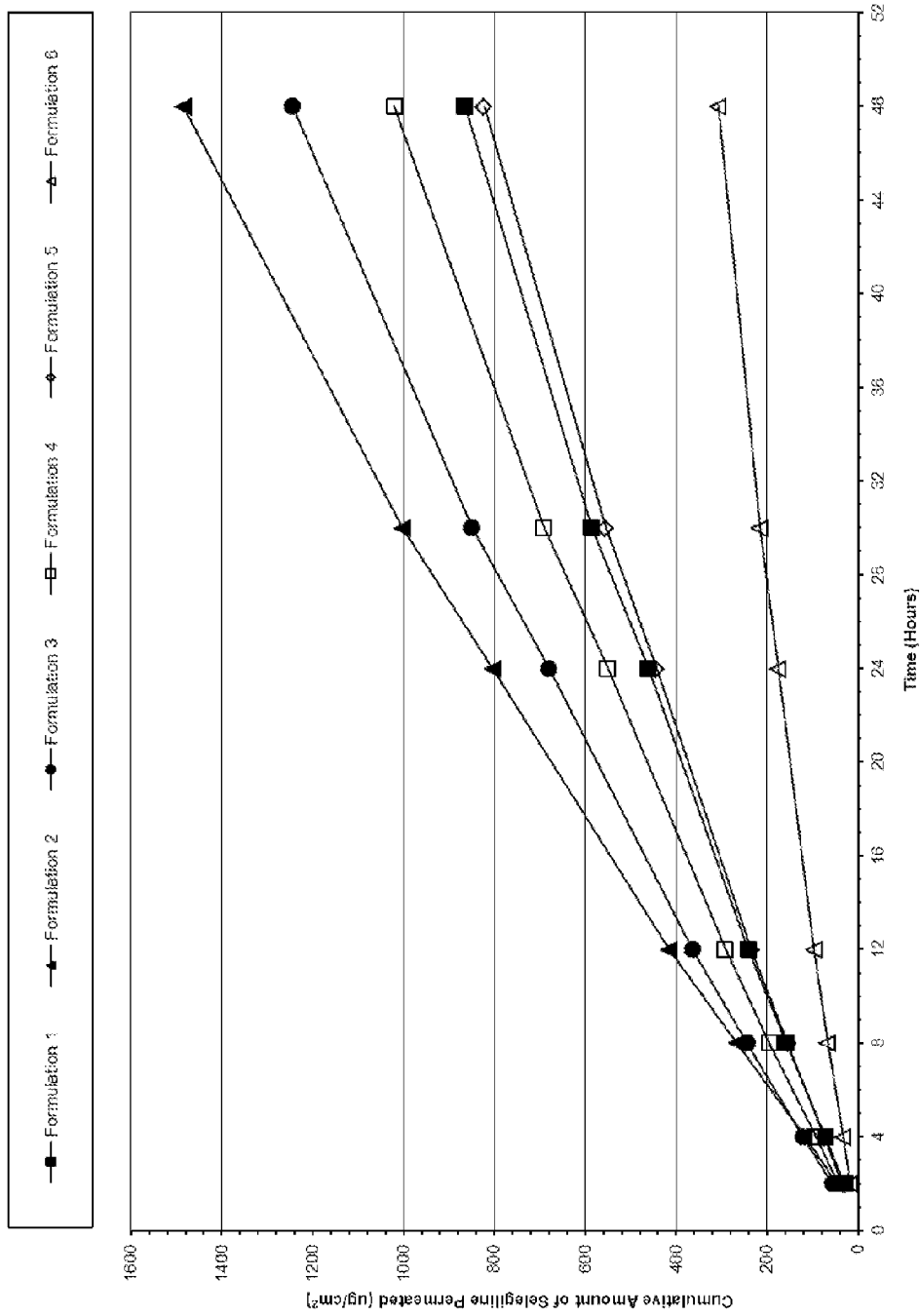

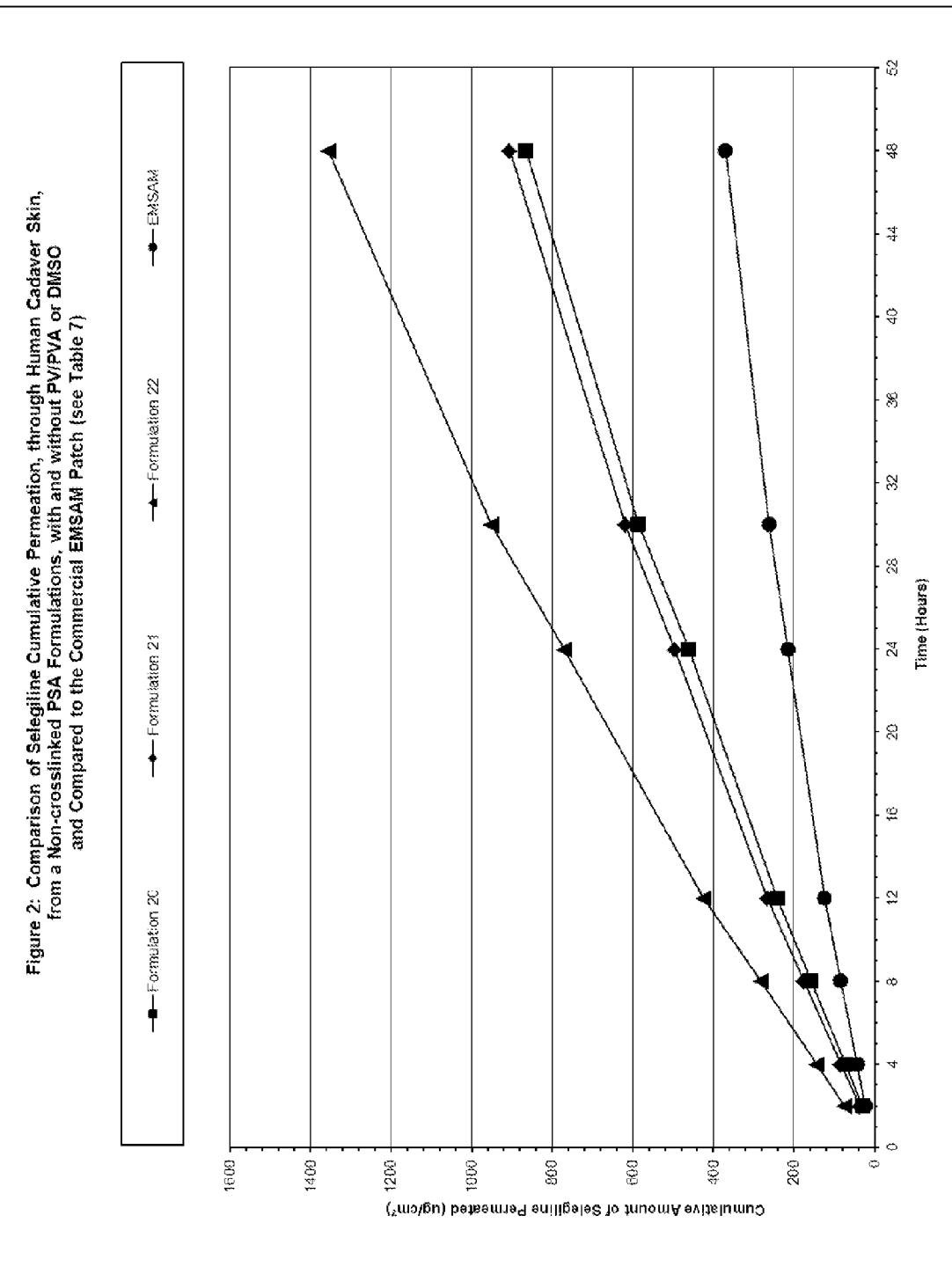

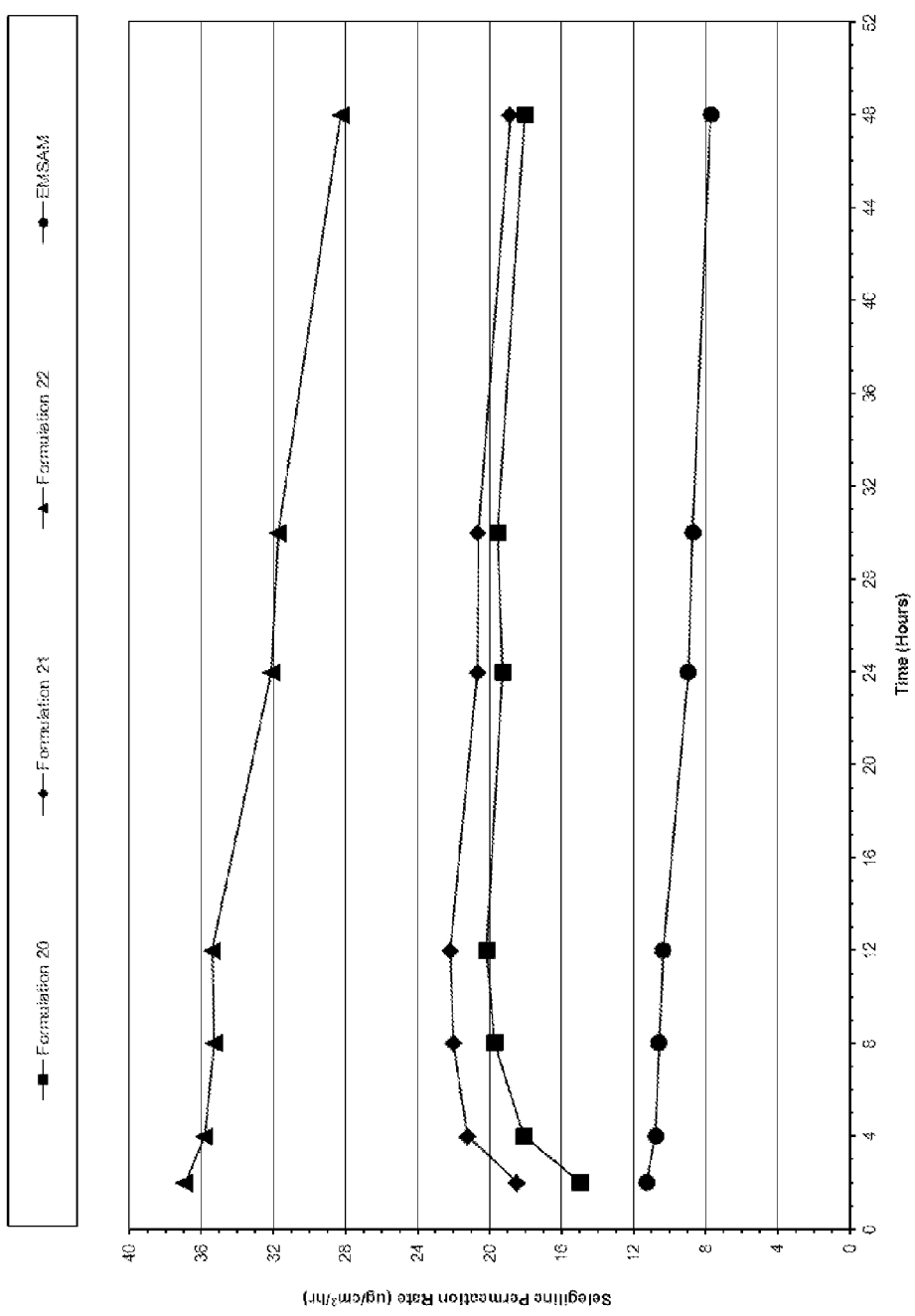

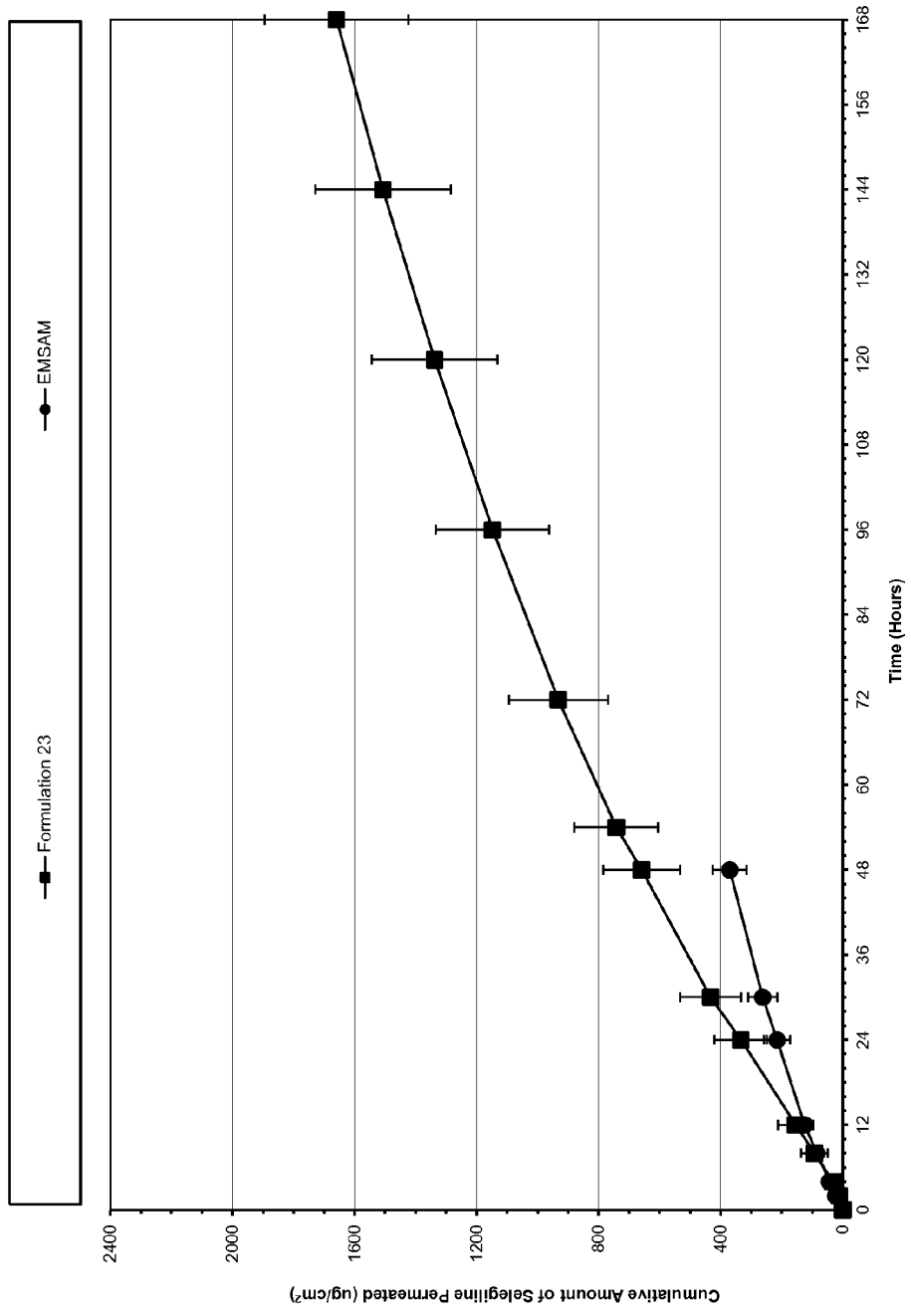

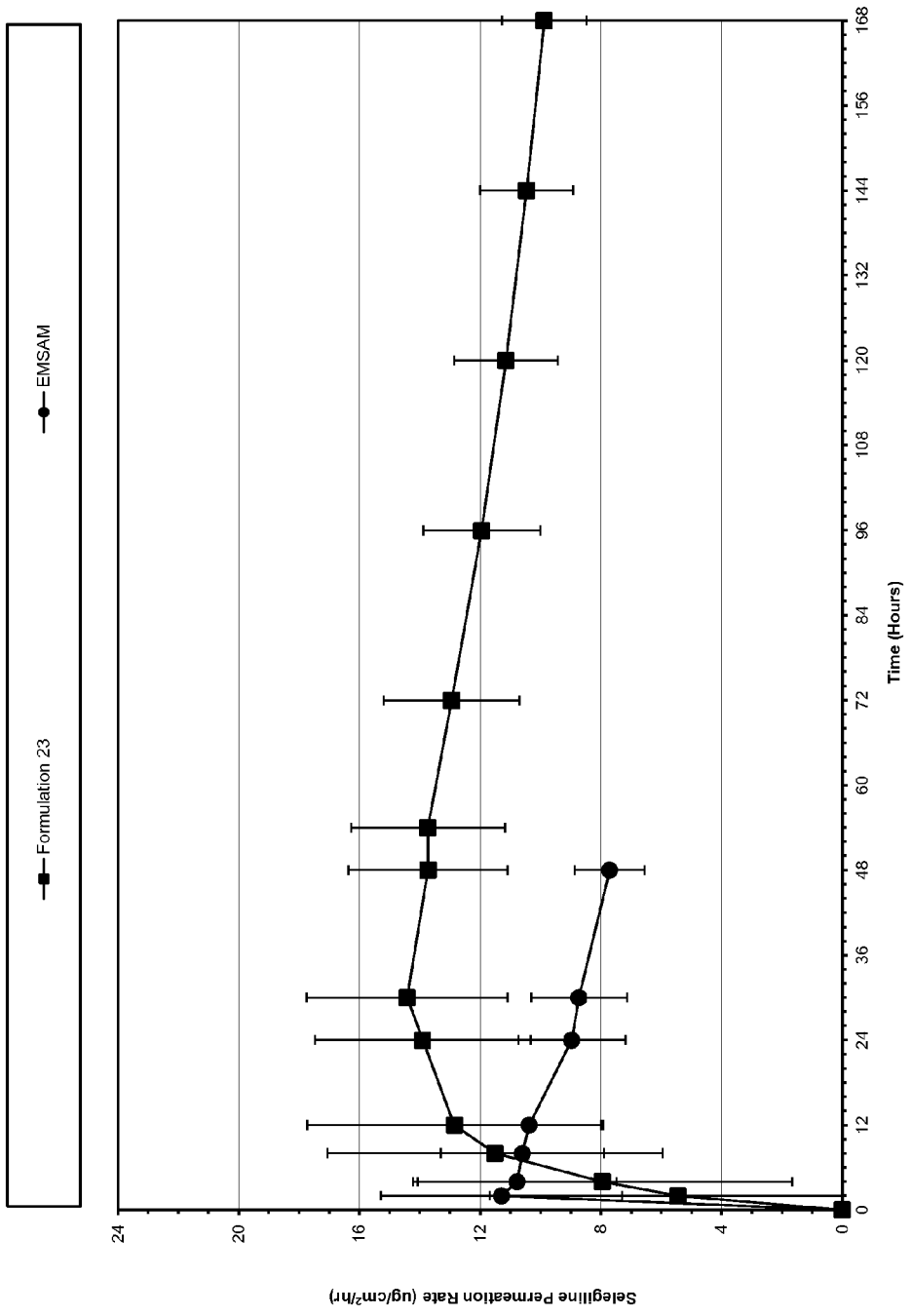

SELEGILINE TRANSDERMAL SYSTEM

CROSS-REFERENCE TO RELATED APPLICATIONS

This application claims the benefit of co-pending U.S. provisional application No. 61/687,215, filed 20 Apr. 2012, which is hereby incorporated herein.

FIELD OF THE INVENTION

This invention relates to the field of transdermal delivery and more specifically to transdermal patches containing selegiline base for the treatment of depression, Parkinson's disease, and other nervous system conditions. In particular the invention provides appropriate pressure sensitive adhesives, humectants and enhancers for the preparation of transdermal selegiline systems.

BACKGROUND OF THE INVENTION

There are many patents pertaining to the delivery of transdermal selegiline to treat many neurologic conditions. US Patent applications 2008/0220092 and 2010/0280432 describe the biosynchonous transdermal delivery of many drugs including selegiline base (selegiline) to take advantage of the body's natural circadian rhythms. U.S. Pat. Nos. 6,461,619 B1, 6,709,664 B2, 7,147,864 B2 disclose the uses of selegiline patches for the treatment of wounds, burns and photodamaged skin. US Patent Application 2007/0212428 A1 describes formulations of drug combinations including selegiline for the treatment of mood spectrum disorders. U.S. Pat. Nos. 6,239,181 B1 and 2001/0023260 teach the use of patches containing selegiline for treating the symptoms associated with peripheral neuropathy.

There are several patents that have issued or are pending pertaining to formulations for transdermal delivery of selegiline and these are more pertinent to our invention. U.S. Pat. No. 6,974,588 B1 describes a four-layer laminated composite, two of the layers being an acrylic PSA and a Silicone PSA attached to each other, both containing the drug. US Patent application 2010/0087768 A1 pertains to acrylic formulations which also include a metal atom and non-volatile adjuvants such as squalene, and triethylcitrate. US Patent Application 2002/0150613 A1 pertains to transdermal patches delivering highly plasticizing drugs such as selegiline by providing the drug in protonated form together with a strong deprotonating agent, such as diethylamine, which subsequently deprotonates the drug to selegiline free base, which is more permeable through the skin. U.S. Pat. Nos. 7,070,808 B2 and 7,638,140 B2 describe formulations and production methods that can accommodate highly plasticizing drugs such as selegiline and/or the use of protonated forms of drugs in general by using acrylic adhesives containing functional groups for crosslinking and crosslinking agents. U.S. Pat. No. 7,150,881 B2 pertains to selegiline transdermal systems comprising acrylic adhesives free of liquids and humectant/solubilizers with very specific conditions of processing. The last three patents are the basis of a commercial transdermal patch marketed as an antidepressant under the name of EMSAM. EMSAM is available in three sizes, 20 mg/20 $cm^2$, 30 mg/30 $cm^2$ and 40 mg/40 $cm^2$ that deliver on average 6 mg, 9 mg and 12 mg respectively of selegiline over 24 hours.

SUMMARY OF THE INVENTION

As mentioned in the Background section above, formulations for the transdermal delivery of selegiline from acrylic pressure sensitive adhesive formulations (PSA), needed to use acrylic adhesives with functional groups and/or crosslinkers to crosslink the acrylic polymer so as to provide the ability of the acrylic matrix to hold the liquid selegiline drug without syneresis and to provide good adhesion to skin for at least one day as is the case with the commercial product EMSAM. For example, acrylic pressure sensitive adhesives disclosed include Duro-Tak 87-2516, 87-2852 and 87-2194. All three pressure sensitive adhesives contain hydroxyl or carboxyl functional groups and crosslinking agents. Crosslinkers disclosed include butyl titinate, aluminum isopropoxide, aluminum zinc acetate, multivalent metals, ureas and melamines. Some of the patents specifically exclude organic solvents, volatile components and humectants/solubilizers such as polyvinyl pyrrolidone (PVP) and polyvinyl pyrrolidone vinyl acetate copolymers (PVP/VA). We have found out that some acrylic pressure sensitive adhesives that do not contain functional groups and or crosslinkers including metals, have the ability to solubilize large amounts of selegiline without causing syneresis and which have very good adhesive properties to skin. In contrast to prior art we also found that the use of humectant/solubilizers such as PVP and PVP/VA stabilize acrylic pressure sensitive adhesives that do not contain functional groups and/or crosslinkers and allow the preparation of transdermal formulations of selegiline that do not have problems with syneresis or adhesion to skin and provide excellent permeation through human skin.

BRIEF DESCRIPTION OF THE DRAWINGS

FIG. 1. Average cumulative amount of selegiline (three diffusion cells per formulation) permeated through human skin over a period of two days, from three non-crosslinked and three crosslinked acrylic PSA formulations (see Example 1)

FIG. 2. Average cumulative amount of selegiline (three diffusion cells per formulation) permeated through human skin over a period of two days, from three preferred formulations of our invention and EMSAM, a commercial product delivering selegiline base for the treatment of depression (see Example 7).

FIG. 3. Average skin diffusion rate of selegiline (three diffusion cells per formulation) through human skin over a period of two days, from three preferred formulations of our invention and EMSAM, a commercial product delivering selegiline base for the treatment of depression (see Example 7).

FIG. 4. Average cumulative amount of selegiline (ten diffusion cells for the unenhanced formulation and three for EMSAM) permeated through human skin from an unenhanced formulation of our invention for a period of seven days and EMSAM a commercial product delivering selegiline base for the treatment of depression (see Example 8).

FIG. 5. Average skin diffusion rate of selegiline (ten diffusion cells for the unenhanced formulation and three for EMSAM) through human skin from an unenhanced formulation of our invention for a period of seven days and EMSAM a commercial product delivering selegiline base for the treatment of depression (see Example 8).

DETAILED DESCRIPTION OF ILLUSTRATIVE EMBODIMENTS

The invention pertains to the transdermal delivery of selegiline for the treatment of depression, Parkinson's disease and other neurologic conditions. The first embodiment pertains to the use of acrylic pressure sensitive adhesives which do not contain functional groups and which are not crosslinked, but are able to absorb large amounts of selegiline without syneresis and at the same time provide equal or better adhesion to skin and permeation through human skin than inventions of the prior art. Acrylic pressure sensitive adhesives (PSAs) that could be used with the invention include those based on pure acrylate monomers as well as acrylate copolymers and terpolymers using for example as the comonomers vinyl acetate or hydrocarbon copolymers which may also include pacifiers and other pressure sensitive adhesive modifiers. Commercially available acrylate copolymers include those made by Henkel Corporation under the trade names of Duro-Tak 87-900A (DT 87-900A), 87-901A, 87-9301, 87-9088, and 87-4098. These copolymers do not contain functional groups or crosslinkers. Of specific interest is the pressure sensitive adhesive DT 87-4098 which is the only copolymer mentioned above that contains vinyl acetate and which has low levels of peel, shear and tack which can then be enhanced by the incorporation of large amounts of plasticizing liquids such as selegiline. Since these polymers are not crosslinked, the resistance of movement of the drug through the patch itself will be very low thus enhancing the permeability through human skin. Thus it is an object of our invention to use non-crosslinked acrylate copolymer PSAs in matrix selegiline patches, especially PSA DT 87-4098, to provide for excellent permeation of selegiline through human skin. Another object of our invention is to use humectant/solubilizers in the matrix patch to provide for stabilization of the patch through absorption and immobilization of the liquids in the patch. For example such humectant/solubilizers include PVP, PVP/VA, hydroxypropylcellulose, hydroxyethylcellulose, hydroxypropylmethylcellulose, methyl cellulose, Sodium carboxymethyl cellulose, colloidal silica, Xantham Gum, and polyacrylic acid. By experiment we determined that the best humectant/solubilizer for matrix patches delivering selegiline is PVP/VA. PVP/VA has the ability to properly disperse/solubilize within the PSA matrix and to provide additional stability to the matrix, absorb the liquid selegiline base and prevent syneresis. In prior art, PVP was specifically excluded from the use in selegiline patches, which in our case, where we use non crosslinked acrylic PSAs, are shown to be very important to the development of a patch of our invention. It is another object of our invention to incorporate in the matrix PSA humectant/ solubilizers, and especially PVP/VA, in the amounts of between 3 to 30% on the weight of the PSA, to provide for better syneresis, adhesion to skin and more rapid permeation of the drug through the skin. The ability of the composition of our patch is such that volatile and non-volatile enhancers can be included in the formulations, which are specifically excluded in the prior art Volatile enhancers for the case of our invention are liquids that have a vapor pressure at 20 degrees Centigrade which is higher than 0.2 mm Hg. Volatile enhancers such as Dimethylsulfoxide (DMSO), decylmethylsulfoxide lactates such as ethyl lactate and propyl lactate isobutyl lactate and lauryl lactate can be incorporated in the PSA matrix system of the selegiline patch of our invention. Thus it is another object of our invention to incorporate volatile enhancers in our patch so as to increase the permeation of selegiline through the human skin and reduce the size of the patch. Non-volatile enhancers, such as lauryl lactate can also be incorporated but the level of these enhancers will need to be controlled very closely, because they have the ability to increase the potential of syneresis or form very soft adhesives that will leave residue on the skin upon removal. The selegiline patches that are commercially available have to be changed daily. It is another object of our invention to manufacture patches that would need to be changed only twice per week. The ability of our patches to contain a large volume of selegiline and release it on demand, allows for the delivery of selegiline through human skin in pseudo-zero order for a much longer period of time, as it will be shown in the examples below. Since the loss of selegiline over a several day period is large, as much as 150 mgs per 3 and a half day wear, the adhesion to skin might be compromised for several of the formulations of our invention. In such a case a peripheral adhesive can be used around the periphery of the active patch to give extra adhesive strength to the skin. The peripheral adhesive should preferentially be composed of a polymer into which selegiline is not highly soluble. For example the solubilities of selegiline in the non-crosslinked acrylic copolymers PSAs DT 87-9088, DT 87-9301 and DT 87-4098 are respectively 118, 81 and 59 wt % versus that in polyisobutylene (PIB) and silicone PSAs which are respectively 8 and 6 wt %. Therefore, peripheral adhesive formulations comprising PIB and silicone PSAs will be excellent for the application.

The patch of our invention will in general be composed of three layers, a backing layer such as Scotchpak 9733 (2 ml thick), provided commercially by 3M. Scotchpak 9733 comprises a polyester polymer film with a tie layer of ethylene vinyl acetate coated onto the polyester film. The tie layer provides good adhesion to the active polymer layer which comprises the acrylic adhesive of our invention and the selegiline base. To the top portion of the active polymer layer is attached a release liner which is removed and disposed just prior to the application of the patch to the human body. The release liner can be made of paper or polymer film such as a polyester polymer film, coated with a silicone or fluoropolymer release coating. Such release liners are commercially provided by 3M, Saint Cobain and Loparex. In the experimental work presented in the examples below, the release liner was Scotchpak 9742 (4.6 mil thick). In the case a peripheral adhesive is required this will be applied on the back side of the backing layer and extending beyond the backing layer on all four sides by at least one eighth of an inch.

EXAMPLES

Example 1

In this example, experiment work was performed to determine if there is a difference between crosslinked and non-crosslinked acrylic pressure sensitive adhesives as claimed in the patent literature. Three non-crosslinked adhesives DT 87-9088, DT 87-9301 and DT 87-4098 and three crosslinked adhesives DT 87-2194, DT 87-2516 and DT 87-2852 were used to prepare transdermal patches. The respective PSA adhesives were coated onto the Scotchpak 9733 and dried in the oven at 70 degrees centigrade for 10 minutes, at which time the release liner Scotchpak 9742 was applied on the exposed PSA side. The coating equipment used was a Warner Mathis Lab Coater, Drying Oven Model (Model LTF, S/N 124188, Coater Model LTSV, S/N 75288). The thickness of the dried patches (active adhesive portion) was between 4 and 5 mils. The selegiline loss during drying was between 20 and 30%. Due to this high loss all subsequent experiments presented in the following examples were performed at 60 degrees Centigrade for 10 minutes (drug loss between 10 and 20%). Skin flux studies through human skin were also performed using Franz diffusion cells in triplicate for each patch, with the receptor medium being phosphate buffered saline pH 7.4. Samples from the receptor phase were obtained at the time intervals of 2, 4, 8, 12, 24, 30, and 48 hours and the selegiline that permeated through the skin was quantified using HPLC. The adhesive properties were determined by physical examination of the patches. All of the data are summarized in Table 1. FIG. 1 shows the cumulative amount of selegiline permeated through human skin over a two day period for all patches comprising the six adhesives. To our surprise no difference was seen in the patches comprising crosslinked or non-crosslinked acrylic PSA adhesives, both from the adhesive properties point of view or from the flux through skin. Syneresis was not observed in any of the patches, which was one major concern when the experimentation was initiated. Since we did not see much difference in the use of any of the acrylic PSAs, all experimental work shown in examples 2 through 7 used the acrylic PSA DT 87-4098. The inventors had prior experience (e.g. WO 2009/009649, WO 2009/009651, U.S. Pat. No. 7,045,145 B1) with DT 87-4098 which has the ability to contain up to 25% enhancers without syneresis.

TABLE 1

Comparison of Selegiline Permeation through Human Cadaver Skin From Crosslinked and Non-crosslinked Acrylic PSA Patches

| | Experiment # | | | | | |
|---|---|---|---|---|---|---|
| | 1 | 2 | 3 | 4 | 5 | 6 |
| Selegiline base | 13.5% | 21.8% | 16.9% | 18.6% | 11.4% | 10.1% |
| DT 87-4098 | 86.5% | | | | | |
| DT 87-9088 | | 78.2% | | | | |
| DT 87-9301 | | | 83.1% | | | |
| DT 87-2194 | | | | 81.4% | | |
| DT 87-2516 | | | | | 88.6% | |
| DT 87-2852 | | | | | | 89.9% |
| Total | 100% | 100% | 100% | 100% | 100% | 100% |
| Functional Group | No | No | No | Yes | Yes | Yes |
| Crosslinker | No | No | No | Yes | Yes | Yes |
| Average Flux, mcg/cm$^2$/hr | 19.6 | 34.5 | 28.2 | 23.1 | 18.6 | 7.2 |
| Adhesion Comments | A | B | B | B | C | A |

A = Very Good Adhesion; No Residue
B = Excellent Adhesion; Some Residue
C = Excellent Adhesion; Difficult to Release from Release Liner Example 2

In this example the effect of addition to the formulations of our invention of excipients that are humectant/solubilizers was investigated. These compounds, such as PVP/VA, are able to absorb moisture released through the skin by transepidermal water loss (TEWL) and thus minimize irritation in the area covered by the patch. Secondly, PVP/VA improves adhesion of the patch to the skin by absorbing the TEWL and not allowing the moisture to accumulate at the skin/patch interface and thus break the adhesive bond. Previous patents on selegiline specifically excluded the use of such compounds including PVP.

The experiment was performed essentially as described in example 1 and the results are shown in Table 2. It is obvious from the data that PVP/VA does not have any adverse effects on the permeation of the selegiline through human skin, or on the adhesive properties of patches containing the PVP/VA.

TABLE 2

Comparison of Selegiline Permeation through Human Cadaver Skin from a Non-crosslinked Acrylic PSA Adhesive with and without PVP/VA, as an Adhesion Promoter and Moisture Absorber

| | Experiment # | |
|---|---|---|
| | 7 | 8 |
| Selegiline base | 13.5% | 11.3% |
| PVP/VA | 0.0% | 19.6% |
| DT 87-4098 | 86.5% | 69.1% |
| Total | 100% | 100% |
| Functional Group | No | No |
| Crosslinker | No | No |
| Average Flux, mcg/cm$^2$/hr | 19.6 | 20.8 |
| Adhesion Comments | A | A |

A = Very Good Adhesion; No Residue

Example 3

This experiment was performed to determine the performance of transdermal patches containing different concentrations of selegiline. Three patches were prepared essentially as described in example 1 with 13.5, 16.2 and 29.4% selegiline. The flux through human skin and the adhesive properties were determined as described in the above examples. The formulations and data are shown in Table 3. It is obvious from the data that as expected, the flux increased with increase in selegiline concentration in the patch. The adhesive properties were not acceptable at the high concentrations of selegiline and it appears that a maximum concentration of selegiline in a patch composed of selegiline and DT 87-4098 is about 15%.

TABLE 3

Comparison of Selegiline Permeation Through Human Cadaver Skin From a Non-crosslinked Acrylic PSA Adhesive as a Function of Selegiline Concentrations

| | Experiment # | | |
|---|---|---|---|
| | 9 | 10 | 11 |
| Selegiline base | 13.5% | 16.2% | 29.4% |
| DT 87-4098 | 86.5% | 83.8% | 70.9% |
| Total | 100% | 100% | 100% |
| Functional Group | No | No | No |
| Crosslinker | No | No | No |
| Average Flux, mcg/cm$^2$/hr | 19.6 | 26.5 | 46.2 |
| Adhesion Comments | A | B | C |

A = Very Good Adhesion; No Residue
B = Good Adhesion; Some Residue
C = Not Acceptable; Adhesive Stringiness; Residue Example 4

This experiment was performed to determine the effect of concentration of selegiline on the flux and adhesion properties of patches containing DT 87-4098 and PVP/VA at an amount of 20% which is a level commonly used in the preparation of transdermal patches. The patches were manufactured essentially the same way as discussed in example 1. The results are shown in Table 4 and indicate that the flux can be increased in this type of formulation by small increases in selegiline concentration. The adhesion was very good and again it indicates that for the specific formulations, the maximum selegiline concentration is about 15%.

TABLE 4

Comparison of Selegiline Permeation through Human Cadaver Skin from a Non-crosslinked Acrylic PSA Adhesive with PVP/VA, as a Function of Selegiline Concentration

|  | Experiment # | |
|---|---|---|
|  | 12 | 13 |
| Selegiline base | 11.3% | 12.7% |
| PVP/VA | 19.6% | 19.6% |
| DT 87-4098 | 69.1% | 67.7% |
| Total | 100% | 100% |
| Functional Group | No | No |
| Crosslinker | No | No |
| Average Flux, mcg/cm$^2$/hr | 20.8 | 25.9 |
| Adhesion Comments | A | B |

A = Very Good Adhesion; No Residue
B = Good Adhesion; Residue at the Edge of Patch on Application; No Residue after Removal

Example 5

This Example provides selegiline formulation comprising DT 87-4098, 20% PVP/VA with and without the incorporation of the non-volatile enhancer Lauryl lactate (Ceraphyl 31). In our patent non-volatile enhancers are defined as those that have a vapor pressure at 20 degrees Centigrade which is less than 0.2 mm Hg. It is obvious from the data shown on Table 5 that both formulations that contained Ceraphyl 31 were not acceptable since they showed stringiness and residue upon removal of the patch. It can be concluded here that non-volatile liquid enhancers (or other excipients) can be used as long as the percentage of the enhancer plus the percentage of selegiline does not exceed approximately 15%.

TABLE 5

Comparison of Selegiline Permeation Through Human Cadaver Skin from a Non-crosslinked Acrylic PSA Adhesive PVP/VA and Non-volatile Enhancer (Lauryl Lactate)

|  | Experiment # | | |
|---|---|---|---|
|  | 14 | 15 | 16 |
| Selegiline base | 12.7% | 12.6% | 20.5% |
| PVP/VA | 19.6% | 20.0% | 20.0% |
| Ceraphyl 31 | 0.0% | 5.0% | 5.0% |
| DT 87-4098 | 67.7% | 62.4% | 54.5% |
| Total | 100% | 100% | 100% |
| Functional Group | No | No | No |
| Crosslinker | No | No | No |
| Average Flux, mcg/cm$^2$/hr | 25.9 | 20.7 | 33.8 |
| Adhesion Comments | A | B | B |

A = Good Adhesion; Trace Residue at the Edge of Patch on Application
B = Very Good Adhesion; Stringiness and Residue on Patch Application and Removal

Example 6

This Example shows the composition of three formulations comprising DT 87-4098, 20% PVP/VA with and without a volatile enhancer (or other excipient). In this case the volatile enhancer/excipient was DMSO with a vapor pressure at 20 degrees Centigrade of 0.417 mm Hg. The flux and adhesion properties are shown in Table 6. It is obvious from the data that all formulations are acceptable from the adhesion point of view and that the inclusion of volatile enhancers/excipients has a positive impact on the penetration of selegiline through human skin. In conclusion, volatile enhancers or excipients can be included in formulation of selegiline at levels whereby the percentage of selegiline plus the percentage of the volatile.

TABLE 6

Comparison of Selegiline Permeation through Human Cadaver Skin from a Non-crosslinked Acrylic PSA Adhesive containing PVP/VA and a Volative Enhancer (DMSO)

|  | Experiment # | | |
|---|---|---|---|
|  | 17 | 18 | 19 |
| Selegiline base | 11.2% | 12.1% | 12.5% |
| PVP/VA | 20.0% | 20.0% | 20.0% |
| DMSO | 0.0% | 10.0% | 5.0% |
| DT 87-4098 | 68.8% | 57.9% | 62.5% |
| Total | 100% | 100% | 100% |
| Functional Group | No | No | No |
| Crosslinker | No | No | No |
| Average Flux, mcg/cm$^2$/hr | 24.5 | 29.7 | 31.6 |
| Adhesion Comments | A | B | B |

A = Excellent Adhesion; Slight Residue at the Edge
B = Excellent Adhesion; Stringiness and Residue After Application; Acceptable Residue Upon Removal

Example 7

This Example compares three preferred compositions of our invention with that of a commercial product, EMSAM, also delivering selegiline base. All samples including EMSAM had very good adhesive properties and delivered selegiline base through human skin (see Table 7). However, the delivery of selegiline from the patches of our invention had at least double the rate of delivery of selegiline when compared to the commercial product. See FIGS. 2 and 3 illustrating respectively the cumulative amount of selegiline released over a two day period and the diffusion rate (flux) of selegiline through human skin over that same period of two days.

TABLE 7

Comparison of Selegiline Permeation through Human Cadaver Skin from a Non-crosslinked Acrylic PSA Adhesive with and without PVP/VA or DMSO and compared to the Commecial EMSAM Patch

|  | Experiment # | | | |
|---|---|---|---|---|
|  | 20 | 21 | 22 | EMSAM |
| Selegiline base | 13.5% | 11.3% | 12.5% |  |
| PVP/VA | 0.0% | 19.6% | 20.0% |  |
| DMSO | 0.0% | 0.0% | 5.0% |  |
| DT 87-4098 | 86.5% | 69.1% | 62.5% |  |
| Total | 100% | 100% | 100% |  |
| Functional Group | No | No | No | Yes |
| Crosslinker | No | No | No | Yes |
| Average Flux, mcg/cm$^2$/hr | 19.6 | 20.8 | 31.6 | 8.7 |
| Adhesion Comments | A | A | B | A |

A = Very Good Adhesion; No Residue
B = Excellent Adhesion; Stringiness and Residue after Application; Acceptable Residue Upon Removal

Example 8

This Example shows the ability of an unenhanced formulation of our invention Formulation 23-7.9% selegiline+ 20.0% PVP/VA+72.1% Duro-Tak 87-4098 to deliver therapeutics levels of selegiline over a seven day period. In contrast, the commercial EMSAM patch is already declining after 24 hours. Duro-Tak 87-4098 has no functional group and has no crosslinker. The patch had very good adhesion and no residue on the skin. This patch had an average flux (0 to 168 hr) of 9.9 mcg/cm$^2$/hr and the EMSAM patch had an average flux (0 to 24 hr) of 8.7 mcg/cm$^2$/hr. In conclusion, the patch formulation of our invention delivers a consistent amount of selegiline over 3.5 days and selegiline therapeutic levels over 7 days (see FIG. 4 and FIG. 5).

What is claimed is:

1. A transdermal matrix patch comprising:
   an acrylate copolymer pressure sensitive adhesive which contains vinyl acetate and does not contain any functional groups or crosslinking agents;
   polyvinyl pyrrolidone vinyl acetate copolymers (PVP/VA) at a concentration of about 20 wt %;
   a volatile or non-volatile liquid enhancer at a concentration of 15 wt % or less; and
   a quantity of selegiline,
   wherein the transdermal matrix patch is capable of delivering the quantity of selegiline over a period of up to about seven days and at a rate of at least about 12 µg/cm$^2$/hour over a period of at least the first 48 hours.

2. The transdermal matrix patch of claim 1, wherein the enhancer is selected from a group consisting of: DMSO, decylmethylsulfoxide, and a lactate ester.

3. The transdermal matrix patch of claim 2, wherein the lactate ester is lauryl lactate.

4. The transdermal matrix patch of claim 1, wherein the enhancer is a non-volatile enhancer and the total percentage of the selegiline plus the non-volatile enhancer does not exceed 15% of the weight of the active patch formulation.

5. The transdermal matrix patch of claim 1, wherein the transdermal patch is capable of delivering the quantity of selegiline at a rate of at least about 16 µg/cm$^2$/hour over the period of at least the first about 48 hours.

6. The transdermal matrix patch of claim 1, wherein the transdermal patch is capable of delivering the quantity of selegiline at a rate of at least about 24 µg/cm$^2$/hour over the period of at least about 48 hours.

* * * * *